United States Patent
Benesova et al.

(10) Patent No.: US 7,384,919 B2
(45) Date of Patent: Jun. 10, 2008

(54) INCREASED SOLUBILITY FLAVANOLIGNAN PREPARATIONS

(75) Inventors: Kvetoslava Benesova, Opava (CZ); Ladislav Cvak, Opava (CZ); Milan Stuchlik, Opava (CZ)

(73) Assignee: IVAX Pharmaceuticals s.r.o. (CZ)

( * ) Notice: Subject to any disclaimer, the term of this patent is extended or adjusted under 35 U.S.C. 154(b) by 80 days.

(21) Appl. No.: 10/487,651

(22) PCT Filed: Aug. 30, 2002

(86) PCT No.: PCT/US02/27713

§ 371 (c)(1),
(2), (4) Date: Dec. 2, 2004

(87) PCT Pub. No.: WO03/020291

PCT Pub. Date: Mar. 13, 2003

(65) Prior Publication Data

US 2005/0101546 A1    May 12, 2005

(30) Foreign Application Priority Data

Aug. 30, 2001 (CZ) ................... 2001-3153

(51) Int. Cl.
*A61K 31/70* (2006.01)
*A61K 31/335* (2006.01)
*A61K 31/35* (2006.01)
(52) U.S. Cl. ............ 514/22; 514/452; 514/456
(58) Field of Classification Search ............... None
See application file for complete search history.

(56) References Cited

U.S. PATENT DOCUMENTS 4,081,529 A * 3/1978 Crippa .................. 514/452
4,764,508 A * 8/1988 Gabetta et al. ............. 514/78
4,886,791 A * 12/1989 Giorgi et al. ............. 514/100
4,895,839 A    1/1990 Bombardelli et al.
5,019,562 A * 5/1991 Folkman et al. ............ 514/58
5,196,448 A    3/1993 Ely
5,198,430 A * 3/1993 Valcavi et al. ............ 514/58
5,906,991 A * 5/1999 Wachter et al. ........... 514/452

FOREIGN PATENT DOCUMENTS

| CZ | 287 657 | 12/1997 |
| EP | 0 722 719 | 7/1996 |
| WO | WO-99/18985 | 4/1999 |

OTHER PUBLICATIONS

Morazzoni et al., "*Silybum marianum (Carduus marianus)*", Fitoterapia, LXVI, 3-42, (1995).
Saller et al., "The Use of Silymarin in the Treatment of Liver Diseases", Drugs, 61:2035-2063 (2001).
Wellington et al., "Silymarin: A Review of its Clinical Properties in the Management of Hepatic Disorders", BioDrugs, 15(7): 465-489, (2001).
Pharm. Forum, "Powdered Milk Thistle Extract", 28; 418-420, (2002).
Comoglio A., et al., "Scavenging the Effect of Silipide, A New Silybin-Phospholipid Complex, On Ethanol-Derived Free Radicals", BioChem. Pharmacol., 50:(8):1313-1316(1995).

* cited by examiner

*Primary Examiner*—Raymond J. Henley, III
(74) *Attorney, Agent, or Firm*—Lerner, David, Littenberg, Krumholz & Mentlik, LLP

(57) ABSTRACT

The inventors have devised novel approaches for the preparation of flavanolignan compositions of enhanced solubility and substantially free of toxic contaminants. Such novel approaches are based on spray drying or lyophilizing to dry a diluted preparation of flavanolignan. These approaches avoid the use of toxic excipients and or carriers commonly used to precipitate flavanolignan concentrates and thus address the drawbacks of existing methods and compositions.

24 Claims, No Drawings

INCREASED SOLUBILITY FLAVANOLIGNAN PREPARATIONS

BACKGROUND OF THE INVENTION

1. Field of the Invention

The invention relates to compositions and a process for the manufacture of a flavanolignan-containing substance from milk thistle displaying enhanced aqueous solubility relative to pure flavanolignan preparations. The substance of the method according to the invention is useful for the manufacture of solid medicinal products and dietary supplements with desired improved dissolution characteristics.

2. Summary of the Related Art

Fruits of milk thistle (Silybum marianum (L.) Gaertn.) contain several isomeric compounds of flavanol-lignane type of the general formula $C_{25}H_{22}O_{11}$-silybinin A, silybinin B, isosilybinin A, isosilybinin B, silydianin and silychristin—collectively called flavanolignans of milk thistle or silymarin. Silymarin (generally available as the dry extract of milk thistle) has been reported to have numerous pharmacological activities such as for example, antioxidant effect, stabilization of cell membranes, and stimulation of biosynthesis of proteins to mention a few. Silybin (a mixture of silybinin A and silybinin B) has been found to be particularly suited as an hepatoprotective agent. Silymalin is effective in the treatment and prophylaxis of liver disease including acute and chronic intoxication of the liver caused by toxins, (including drugs and various alcohols, e.g., carbon tetrachloride, galactosamine, paracetamol, ethanol, phalloidin and α-amanitin). Silymarin is an active component of pharmaceutical products, (e.g., LEGALON®, Madus AG, Koln, Germany; Hepamarin, Pharmasan GmbH, Freiburg, Germany; HEPADURAN®, Zwinkscher GmbH, Karlsruhe, Germany; or SILYHEXAL®, Hexal Pharma AG, Wien, Austria) used to treat and prevent hepatic diseases. More information about silymarin and its use can be found in Morazzoni et al., Fitoterapia, LXVI, 3-42, (1995); Sailer et al., Drugs, 61: 2035-2063, (2001); Wellington et al., BioDrugs, 15(7): 465-489, (2001).

The silymarin preparation used for manufacture of pharmaceutical preparations or food supplements is thus a purified extract standardized to include specific flavanolignans. Pharm. Forum 28: 418-420, (2002) provides that silymarin contains not less than 90% and not more than 110% of silymarin, calculated as silybin on the dried basis; consisting of not less than 20.0% and not more than 45.0% of the sum of silydianin and silycristin; not less than 40% and not more than 65% for the sum of silibin A and silibin B; and not less 10.0% and not more than 20% for the sum of isosilybin A and isosilybin B; contains from about 40 up to 80% flavanolignans consisting of from about 40 up to 65% of the sum of silybinin A and B; from about 20 up to 45% of the sum of silychristin and silydianin and from about 10 up to 20% of the sum of isosilybinin A and B.

However, the use of milk thistle flavanolignans in general and that of silymarin and its components in the preparation of pharmaceutical products is greatly impaired by the low solubility in both hydrophilic and lipophilic environments of these compounds which greatly reduces their bioavailability and resorbability in mammals. Given the tremendous therapeutic potential, it is not surprising that several investigators have sought a variety of approaches to address the solubility/bioavailability problems as attested by the large body of literature on point including several patents discussed hereinafter.

One approach lies in the preparation of silybin esters (mixture of silybinins A and B, possibly also isosilybinins A and B) with dicarboxylic acid. For example U.S. Pat. Nos. 4,895,839 and 5,196,448 describe a di-sodium salt of bis-hemisuccinate of silybin. This preparation is presently incorporated in in LEGALON® SIL inj., a pharmaceutical product for the treatment of serious poisoning by Amanita mushrooms or other hepatotoxic compounds, marketed by Madaus &Co.

Another approach has been the preparation of silybin glycosides as set forth for example in CZ Patent No. 287 657. The described silybin glycosides are more soluble in water than silybin and they show similar effects as silymarin. Complex compounds of silymarin or silybin with phospholipides are also described by U.S. Pat. Nos. 4,764,508 and 4,895,839. These complexes are prepared by dissolution of components (1 mol of silymarin or silybin and 0.3 up to 2.0 mol of phosphatidyl choline, phosphatidyl serine or phosphatidyl ethanolamine) in aprotic solvent (dioxane or acetone) and by precipitation of the complex by addition of aliphatic hydrocarbon or lyophilization or spray drying. The described complex compounds are the basis of the substance called SILIPED™ or SILYPHOS™, (manufactured by Indena) currently under clinical trials (Comoglio A., et al., Biochem. Pharmacol., 50:(8):1313-1316 (1995).

Yet another approach has been formulation in cyclodextrin complexes notorious for their role in solubilizing a variety of compounds. Inclusion complexes of silybinin with cyclodextrines are described in the U.S. Pat. No. 5,198,430. Complexes of silybinin are described with α-, β- and γ-cyclodextrine and their derivatives in molecular ratio of 1 mol of silybinin with 1 up to 4 mol of the corresponding cyclodextrine. Complexes are prepared by dissolution of both components in aqueous ammonia and by removal of the ammonia either by evaporation or neutralization with hydrochloric acid and by subsequent drying or lyophilization.

Solutions of silymarin in polyethylene glycol alone or in polyethylene glycol and some co-solvents and/or surfactants are described in WO 99/18985. The gelatin capsules filled with such solutions show higher solubility in dissolution tests than silymarin alone.

Another patented procedure for increasing the biological availability of silymarin consists in the preparation of coprecipitates of flavanolignans with carriers and detergents (see for example, U.S. Pat. No. 5,906,991 and EP 722719). Suitable carriers according to these methods include water soluble saccharides, derivatives of cellulose and polyvinylpyrrolidone whereas polysorbates of fatty acids are used as detergent. These coprecipitates are said to have higher solubility properties as compared to untreated silymarin. However, some of these obligatory carriers and excipients according to these patents coprecipitate as contaminants with the flavanolignans. Unfortunately, some of these contaminants are known toxic compounds and thus may produce adverse reactions in a patient further exacerbating an already existing condition.

Thus, the currently available approaches for the preparation of flavanolignan compositions suffer from a number of drawbacks. In general, conventional methodologies fail to produce a sufficiently soluble preparation. Moreover, because of the low solubility, such preparations are not sufficiently bioavailable. A further disadvantage of the formulations in presently the art is that often the flavanolignan is bound to a chemical compound which can physiologically act as a foreign substance in the body thereby bringing about undesired side reactions or impair the effectiveness of the flavanolignan. Therefore, there remains a need to identify and develop improved methodologies and compositions. Such methodologies and compositions should overcome the shortcomings of the traditional methods in the literature. It is an object of the present invention to provide flavanolignan preparations which reduce the binding of the flavanolignans to foreign compounds and possess high rate of liberation wherein the liberation is accomplished physically by means of destruction of its crystalline lattice (amorphous substance). These flavanoligaans preparations should maintain their efficacy while limiting their binding to foreign compounds.

SUMMARY OF THE INVENTION

The inventors have devised novel approaches for the preparation of flavanolignan compositions of enhanced solubility and substantially free of toxic contaminants. Such novel approaches are based on spray drying or lyophilizing to dry a diluted preparation of flavanolignan. These approaches avoid the use of toxic excipients and or carriers commonly used to precipitate flavanolignan concentrates and thus address the drawbacks of existing methods and compositions.

The process achieves this advantage through the use of non-toxic water-soluble compounds and spray drying or lyophilizing techniques selected and applied to produce an amorphous product shown to have greater solubility in an aqueous environment. The compositions of the instant invention achieve greater solubility (and thus higher bioavailability) without the need of materials such as wetting agents, or the use of materials such as complexing agents with physiological activity that could result in undesired side reactions or impair the effectiveness of the flavanolignin product.

The patents and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favour of the latter. Likewise, any conflict between an art-understood definition of a word or phrase and a definition of the word or phrase as specifically taught in this specification shall be resolved in favour of the latter.

In one aspect, the invention relates to methods for the preparation of a flavanolignan composition by preparing a solution of an organic solution of one or more flavanolignans, and at least one water-soluble compound, and spray drying or lyophilizing the solution to obtain an amorphous product. In another aspect, the invention provides a dry, amorphous co-precipitate of one or more flavanolignan and at least one sugar alcohol.

These and other features of the invention will be further described and exemplified in the detailed description below.

DETAILED DESCRIPTION OF THE INVENTION

It has now been found, and it constitutes on object of the present invention that the use of spray drying or lyophilizing to prepare flavanolignan compositions results in preparations well suited for pharmacological and nutraceutical uses. The methods and compositions disclosed herein capitalize on the discovery providing much needed preparations which are soluble in a aqueous environment and which are substantially free of potentially toxic contaminants.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics* $10^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference is made in the following description and examples are obtainable from commercial sources, unless otherwise noted.

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details ate set forth in order to provide a thorough understanding of the present invention. The present invention may be practiced without some or all of these specific details. In other instances, well known process operations have not been described in detail in order not to unnecessarily obscure the present invention.

The methods of the present invention are intended for use with any mammal which may experience the benefits of the methods of the invention. Foremost among such effectiveness, although the invention is not intended to be so limited, and is applicable to veterinary uses. Thus, in accordance with the invention, "mammals" include humans as well as non-human mammals, particularly domesticated animals including, without limitation, horses, cows, sheep, dogs, cats, goats, reindeer, and elephants.

It will be understood that the mammal to which a compound of the invention is administered need not suffer from a specific disease state. Indeed, the compounds of the invention may be administered prophylacticly, prior to any development of symptoms. The term "therapeutic," "therapeutically," and permutations of these terms are used to encompass therapeutic, palliative as well as prophilactic uses. Hence, as used herein, by "treating or alleviating the symptoms" is meant reducing, preventing, and/or reversing the symptoms of the individual to which a compound of the invention has been administered, as compared to the symptoms of an individual receiving no such administration.

Surprisingly, it has been found that the solubility of flavanolignans (such as silymarin exemplified hereinafter) is improved as compared to conventional preparations by spray drying or lyophilizing a solution of an organic solution of one or more flavanolignans, and at least one water-soluble compound to obtain an amorphous product. X-ray powder diffraction analysis has shown that soluble flavanolignans preparations tend to be amorphous whereas poorly soluble ones are crystalline in nature. Formulations obtained according to the methods of the invention are preferably a dry-powder form of an amorphous product suitable for pharmacological and nutraceutical uses. Especially preferred flavanolignans according to the invention include silybin, silydianin or silymarin.

An amorphous product prepared by spray drying or by lyophilizing a solution of a flavanolignan (e.g., silymarin) in ethanol, acetone, methanol, isopropylalcohol or ethyl acetate has very low bulk density and is difficult to use. The inventors have discovered that the addition of a water soluble compound, dissolved in water, to an organic solution of one or more flavanolignans (e.g., water-ethanol, water-acetone, water-methanol or water-isopropyl alcohol solutions of silymarin) prior to spray drying or lyophilizing inhibits crystallization thereby producing an amorphous product having the desired solubility properties as discussed above. The addition of a water soluble compound to an organic solution of one or more flavanolignans is postulated to contribute to the higher solubility observed by creating a water-soluble matrix facilitating access of water to the amorphous flavanolignans. Accordingly, one or more flavanolignans are substantially dissolved in an organic solvent and the organic solution is mixed with an aqueous solution containing one or more water-soluble compounds.

In some embodiments of the invention, the flavanolignans solution used for the spray drying comprises about 10 weight parts of one or more flavanolignans dissolved in 30-120 weight parts organic solvent (hereinafter "organic solution"). An aqueous solution containing from about 0.5-10 weight parts of at least one water-soluble compound (hereinafter "aqueous solution") is prepared. The organic solution and aqueous solution are then mixed so that the ratio of flavanolignans and water soluble compounds in the final dry product is in the range of 10: 0.5-10.

Organic solvents according to the invention are non-branched and branched alkanols or ketones having 1-4 carbon atoms, including for example, ethanol, methanol, isopropyl alcohol, water-tert. butanol, acetone, or mixtures thereof.

The inventors have also discovered that flavanolignans' crystallization from the organic-aqueous solution (e.g., water-ethanol, water-acetone, water-methanol or water-isopropylalcohol solution of silymarin) can be reduced by the addition of water-soluble compounds. Contemplated water-soluble compounds include sugar alcohols such as for example, tetritols, pentitols or hexitols (e.g., mannitol, treitol, erytritol, arabinitol, xylitol, talitol, maltitol or sorbitol).

Flavanolignans' compositions (e.g., silybin, silydianin or silymarin) according to the invention will include an amorphous co-precipitate consisting essentially of one or more flavanolignan, and at least one sugar alcohol. In some compositions the alcohol is a tetritol, pentitol or a hexitol. Formulations according to the invention include any composition obtained according to the methods and materials as discussed above.

The methods of the invention do not rely on wetting agents or on complexing agents which may give rise to undesired side reactions or impair the effectiveness of the ultimate flavanolignin-containing product.

The solubility (and possibly the biological availability) of purified components of silymarin, silybin (mixture of silybinin A and silybinin B) or silydianin in water is negligible due to their crystalline :structure. Traditionally these purified compounds are not considered amenable for pharmacological and nutraceutical uses. One of skill will appreciate that it is possible to exploit the present discoveries for the preparation of these purified components where the danger of crystallization in the course of drying is known to be substantially higher than that of flavanolignans solutions.

From a practical standpoint, higher concentrations of inactive components are not desirable for pharmacological and nutraceutical uses insofar as it results in an overall reduced amount of active ingredients on a weight by weight basis. One of skill will realize that an important advantage of the invention lies in the fact that higher solubility is realised by addition of only a relatively small quantity of non-toxic inactive ingredients.

It has been found experimentally that in order to increase the solubility of the solution of flavanolignans, it suffices to add 5% w/w of the final product of the water soluble compounds (e.g., the sugar alcohol described herein). On the other hand, in order to increase solubility of pure flavanolignans (e.g., silybin and silydianin), it is necessary to use higher concentrations of the water soluble compounds (usually at least 30% w/w).

Compositions containing therapeutically effective amounts of the any milk thistle extract prepared according to the invention are useful for the treatment of any mammal affected by any condition responsive to flavanolignan treatment (e.g., diabetes, colon cancer, hypoglycaemia see for example: Marles et al., Phytomedicine 2:137-189, (1995) and Soto et al., Clin. Pharmacology, Toxicology & Endocrinology, 119:125-129, (1998)). Recently, the use of flavanolignans from milk thistle has also been patented as adjuvants in tumour chemotherapy (U.S. Pat. No. 5,714,473) as well as antiproliferative medicines (U.S. Pat. No. 5,912,265).

Additionally, flavanolignans compositions according to the invention may be incorporated in a food supplement such as in nutraceuticals alone or in combination with other active ingredients. For example, flavanolignans compositions may be combined with synergistically acting insoluble fibres from the plant of the family *Amaranthus* and with animal chitosan a well as with soluble fibre from the seeds of *Cyamopsis tetragonoglobulus* (galactomanan guar).

The compositions of the present invention may be provided in a pharmaceutically acceptable vehicle using formulation methods known to those of ordinary skill in the art. The compositions of the invention can be administered by standard routes. The compositions of the invention include those suitable for oral, inhalation, rectal, ophthalmic (including intravitreal or intracameral), nasal, topical (including buccal and sublingual), vaginal, or parenteral (including subcutaneous, intramuscular, intravenous, intradermal, and intratracheal). In addition, polymers may be added according to standard methodologies m the art for sustained release of a given compound.

The formulations of the compositions of the invention may conveniently be presented in unit dosage form and may be prepared by conventional pharmaceutical techniques as discussed above. Such techniques include the step of bringing into association the compound of the invention and the pharmaceutically acceptable carrier(s), such as a diluent or an excipient. In general, the formulations are prepared by uniformly and intimately bringing into association the active ingredient with liquid carriers or finely divided solid carriers or both, and then, if necessary, shaping the product.

Pharmaceutical compositions comprising the compounds of all of the aspects of the present invention suitable for oral administration may be presented as discrete units such as capsules, caplets, gelcaps, cachets, pills, or tablets each containing a predetermined amount of the active ingredient as a powder or granules; as a solution or a suspension in an aqueous liquid or a non-aqueous liquid; or as an oil-in-water liquid emulsion or a water-in-oil emulsion and as a bolus, etc. Alternately, administration of a composition of all of the aspects of the present invention may be effected by liquid solutions, suspensions or elixirs, powders, lozenges, micronized particles and osmotic delivery systems.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

Dosages will depend on the condition being treated, the particular compound of the invention being adminstered, and other clinical factors such as age, weight and condition of the mammal and the route of administration.

The term "therapeutically effective amount" is used to denote treatments at dosages effective to achieve the therapeutic result sought. Furthermore, one of skill will appreciate that the therapeutically effective amount of the compound of the invention may be lowered or increased by fine tuning and/or by administering more than one compound of the invention, or by administering a compound of the invention with other therapeutic modalities. The invention therefore provides a method to tailor the administration/ treatment to the particular exigencies specific to a given mammal. Therapeutically effective amounts may be easily determined for example empirically by starting at relatively low amounts and by step-wise increments with concurrent evaluation of beneficial effect.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein. Such equivalents are considered to be within the scope of this invention, and are covered by the following claims.

EXAMPLES

The starting silymarin in Example 1 had from about 40 up to 80% flavanolignans out of which from about 40 up to 65% was silybinin, about 10 up to 20% isosilybinin and about 20 up to 45% silydianin and silychristin.

Example 1

Preparation of Representative Flavanolignans Compositions Containing Silymarin

Sample 1

80 gms of silymarin were dissolved in 600 ml of absolute ethanol under boiling conditions. 20 gms mannitol were dissolved in 200 ml of water by stirring. The mannitol solution was heated and subsequently added to the silymarin solution by stirring. The solution obtained was kept at the minimum temperature of 75° C. and was gradually spray dried in the stream of hot nitrogen (130-135° C.) on a Buchi Spray Dryer to a substantially dry product.

Sample 2

95 gms of silymarin were dissolved in 600 ml of acetone under boiling conditions. A hot solution of 5 gms sorbitol in 100 ml of water was added to the silymarin solution by stirring. The solution obtained was kept under reflux and was gradually spray-dried (the dryer and conditions as in Sample 1) to obtain a substantially dry product.

Sample 3

90 gms of silymarin were dissolved in 900 ml of methanol under boiling. A hot solution of 10 gms mannitol in 100 ml of water was added to the silymarin solution by stirring. The solution obtained was kept under reflux and was gradually spray-dried (the dryer and conditions as in Sample 1) to obtain a substantially dry product.

Sample 4

85 gms of silymarin were dissolved in 900 ml of isopropylalcohol under boiling. Hot solution of 15 gms xylitol in 100 ml of water was added to the silymarin solution by stirring. The solution obtained was kept at the minimum temperature of 80° C. and was gradually spray-dried (the dryer and conditions as in Sample 1) to a substantially dry product.

Dissolution Tests

To illustrate the desirable characteristics of the flavanolignans compositions of the invention, samples 1 to 4 and the initial silymarin preparation were compared as to their relative solubility by conventional dissolution testing. For this purpose 100 mg of each Samples were filled in hard gelatin capsules (number 00). Individual capsules underwent the test on the device as per the Ph. Eur. Type 2 in 2 litres of the dissolution medium pH 7.5 and under 100 revolutions per minute. Table 1 gives mathematical average values computed from the dissolution of 6 capsules after 30 and 60 minutes.

TABLE 1

| Sample | Dissolution Values | |
|---|---|---|
| | 30 minutes | 60 minutes |
| Silymarin | 41.3% | 45.9% |
| Sample 1 | 82.5% | 88.1% |
| Sample 2 | 77.8% | 83.0% |
| Sample 3 | 79.4% | 81.5% |
| Sample 4 | 83.4% | 85.8% |

Example 2

Preparation of Additional Representative Flavanolignans Compositions From Pure Flavanolignans Sample 1

30 gms of silybin were dissolved in 450 ml of ethanol and heated to boiling. A hot solution of 10 gms sorbitol in 100 ml of water was added to the silybin solution. The solution obtained was kept at the minimum temperature of 75° C. and was gradually dried (the dryer and conditions as in Example 1) on spray dryer to a substantially dry product.

Sample 2

30 gms of silybin were dissolved in 450 ml of ethanol and heated to boiling. A hot solution of 20 gms sorbitol in 100 ml of water was added to the silybin solution. The solution obtained was kept at the minimum temperature of 75° C. and was gradually dried (the dryer and conditions as in Example 1) on spray dryer to a substantially dry product.

Sample 3

30 gms of silybin were dissolved in 450 ml of ethanol and heated to boiling. A hot solution of 30 gms sorbitol in 100 ml of water was added to the silybin solution. The solution obtained was kept at the minimum temperature of 75° C. and was gradually dried (the dryer and conditions as in Example 1) on spray dryer to a substantially dry product.

Sample 4

30 gms of silybin were dissolved in 450 ml of ethanol and heated to boiling. A hot solution of 10 gms manitol in 100 ml of water was added to the silybin solution. The solution obtained was kept at the minimum temperature of 75° C. and was gradually dried (the dryer and conditions as in Example 1) on spray dryer to a substantially dry product.

Sample 5

30 gms of silydianin were dissolved in 350 ml of ethanol and heated to boiling. A hot solution of 10 gms sorbitol in 100 ml of water was added to the silydianin solution. The solution obtained was kept at the minimum temperature of 75° C. and was gradually dried (the dryer and conditions as in Example 1) on spray dryer to a substantially dry product.

Dissolution Tests

Samples 1 to 5 and the initial silybin preparation were tested by conventional dissolution testing as described for Example 1 above. The data are presented in Table 2 below.

TABLE 2

| Sample | Dissolution Values | |
|---|---|---|
| | 30 minutes | 60 minutes |
| Silybin | 4.6% | 4.5% |
| Sample 1. | 85.5% | 84.1% |
| Sample 2. | 79.3% | 83.0% |
| Sample 3. | 82.2% | 81.7% |
| Sample 4 | 87.3% | 85.1% |
| Sample 5 | 89.0% | 84.5% |

Example 3

Preparation of Representative Pharmaceutical Formulations

This example illustrates the preparation of representative hard gelatin capsules comprising flavanolignans compositions according to the invention (e.g., 140 mg of silymarin (as measured by HPLC)).

| Amounts provided for 1000 capsules are as follows: | |
|---|---|
| Powdered extract from milk thistle (as per the example 1, sample 1) | 255.00 g |
| Micro-crystalline cellulose (Avicel PH 302) | 45.00 g |
| Talc | 9.00 g |
| Magnesium stearate | 3.00 g |
| 0.312 g of the homogeneous mixture are filled per capsule. | |

Example 4

Preparation of Representative Nutraceutical Formulations

The instant example illustrates the preparation of representative nutraceutical compositions containing flavanolignans according to the invention. An 8 gms silymarin granulate dose with vegetable fibres is exemplified.

| Powdered extract from milk thistle | | 0.5000 g |
|---|---|---|
| Galactomanan guar | | 2.0000 g |
| Amaranthine fibres | | 2.0000 g |
| Chitosan | | 2.0000 g |
| L-Carnitine tartarate | | 0.7360 g |
| Acesulfam potassium salt | | 0.0640 g |
| Mannitol | up to | 8.0000 g |

The mixture of powders formed by the extract from milk thistle, galactomanan guar, amaranthine fibres and chitosan is granulated with an aqueous solution of L-carnitine tartarate, acesulfam potassium salt and mannitol.

What is claimed is:

1. A method for the preparation of a flavanolignan composition, comprising the steps of:
    (a) providing a solution comprising an organic solution of one or more flavanolignans substantially dissolved in an organic solvent and at least one water-soluble compound, wherein said solution does not comprise a wetting agent or a complexing agent; and
    (b) drying the solution of step (a) to obtain a product which does not comprise a wetting agent or a complexing agent;
wherein the drying is spray drying or lyophilization.

2. The method of claim 1, wherein the solution is dried by spray drying.

3. The method of claim 1, wherein the product is an amorphous product.

4. The method of claim 1, wherein step (a) of providing the solution comprises mixing said organic solution comprising said one or more flavanolignans with an aqueous solution comprising said at least one water-soluble compound.

5. The method of claim 4, wherein the water-soluble compound is a sugar alcohol.

6. The method of claim 4, wherein the sugar alcohol is selected from the group consisting of tetritols, pentitols and hexitols.

7. The method of claim 4, wherein the sugar alcohol is selected from the group consisting of xylitol, mannitol, and sorbitol.

8. The method of claim 4, wherein the solution comprises about 10 weight parts of the organic solution of one or more flavanolignans substantially dissolved in 30-120 weight parts organic solvent mixed with an aqueous solution containing about 0.5-10 weight parts of at least one water-soluble compound, wherein the ratio of flavanolignans and water soluble compounds in the final dry product is in the range of 10:0.5-10.

9. The method of claim 4, wherein the organic solvent is selected from the group consisting of non-branched alkanols, branched alkanols, and ketones, each having 1-4 carbon atoms.

10. The method of claim 4, wherein the organic solvent is selected from the group consisting of ethanol, methanol, isopropylalcohol, water-tert-butanol, and acetone, or a mixture thereof.

11. The method of claim 4, wherein the one or more flavanolignans comprise silybin, silydianin or silymarin.

12. A flavanolignan composition, consisting essentially of a dry, amorphous co-precipitate consisting essentially of one or more flavanolignans and at least one sugar alcohol, wherein each said flavanolignan is a compound of flavanol-lignane type having the general formula $C_{25}H_{22}O_{11}$.

13. The composition of claim 12, wherein the sugar alcohol is selected from the group consisting of tetritol, pentitol and hexitol.

14. The composition of claim 12, wherein each of the one or more flavanolignans is silybin, silydianin or silymarin.

15. A flavanolignan composition prepared according to the method of claim 1, wherein each said flavanolignan is a compound of flavanol-lignane type having the general formula $C_{25}H_{22}O_{11}$.

16. A dry, amorphous co-precipitate consisting essentially of (i) one or more flavanolignans, and (ii) one or more sugar alcohols, wherein each said flavanolignan is a compound of flavanol-lignane type having the general formula $C_{25}H_{22}O11$.

17. The co-precipitate of claim 16, wherein each said sugar alcohol is selected from the group consisting of tetritol, pentitol and hexitol.

18. The co-precipitate of claim 16, wherein each said flavanolignan is silybin, silydianin or silymarin.

19. The composition of claim 14, wherein the one or more flavanolignans comprise silymarin, and wherein the sugar alcohol is mannitol.

20. The composition of claim 19, wherein the composition comprises 5% of said mannitol on a weight by weight basis.

21. The composition of claim 18, wherein the one or more flavanolignans comprise silymarin, and wherein the sugar alcohol is mannitol.

22. The composition of claim 21, wherein the composition comprises 5% of said mannitol on a weight by weight basis.

23. The method of claim 1, wherein the one or more flavanolignans comprise silymarin, wherein the water-soluble compound is mannitol, and wherein the organic solution is ethanol solution.

24. A flavanolignan composition prepared according to the method of claim 23.

* * * * *

UNITED STATES PATENT AND TRADEMARK OFFICE
CERTIFICATE OF CORRECTION

PATENT NO. : 7,384,919 B2
APPLICATION NO. : 10/487651
DATED : June 10, 2008
INVENTOR(S) : Kvetoslava Benesova, Ladislav Cvak and Milan Stuchlik Page 1 of 1

It is certified that error appears in the above-identified patent and that said Letters Patent is hereby corrected as shown below:

Column 4, line 24, replace "ate" with --are--;
Column 6, line 41, replace "m" with --in--;
Column 11, line 16, replace "O11." with --$O_{11}$.--

Signed and Sealed this

First Day of September, 2009

David J. Kappos
*Director of the United States Patent and Trademark Office*